United States Patent [19]

Blechman et al.

[11] Patent Number: 4,671,767
[45] Date of Patent: Jun. 9, 1987

[54] MAGNETIC FORCE FUNCTIONAL ORTHODONTIC APPLIANCES

[75] Inventors: Abraham Blechman, Tappan, N.Y.; Eugene A. Pescatore, Elmwood Park, N.J.

[73] Assignee: Medical Magnetics, Inc., Ramsey, N.J.

[21] Appl. No.: 809,331

[22] Filed: Dec. 16, 1985

Related U.S. Application Data

[63] Continuation-in-part of Ser. No. 693,268, Jan. 22, 1985, Pat. No. 4,593,361.

[51] Int. Cl.⁴ ............................................... A61C 7/00
[52] U.S. Cl. ........................................ 433/19; 433/18
[58] Field of Search ...................... 433/18, 24, 189, 19

[56] References Cited

U.S. PATENT DOCUMENTS 4,396,373  8/1983  Dellinger ................................ 433/6

Primary Examiner—Robert Peshock
Attorney, Agent, or Firm—Hopgood, Calimafde, Kalil, Blaustein & Judlowe

[57] ABSTRACT

Both fixed and removable functional appliances are disclosed employing magnets to provide the requisite force for accomplishing Class II malocclusion correction. Magnets are employed buccally and/or lingually, either operating in sliding or shearing mode or with the inter-pole gap inclined mesio-distally to develop an effective horizontal force component. Long thin rectangular magnets are incorporated bilaterally and inclined mesio-distally in the tooth capping sections of functional type base structures overlying the occlusal surface. Curved or angled straight magnets are located in anterior flanges of functional type base structures for developing horizontal thrust on the mandible. A number of closed magnetic circuits using either low reluctance keepers or shaped magnets are described for providing either increased force or travel or both.

37 Claims, 38 Drawing Figures

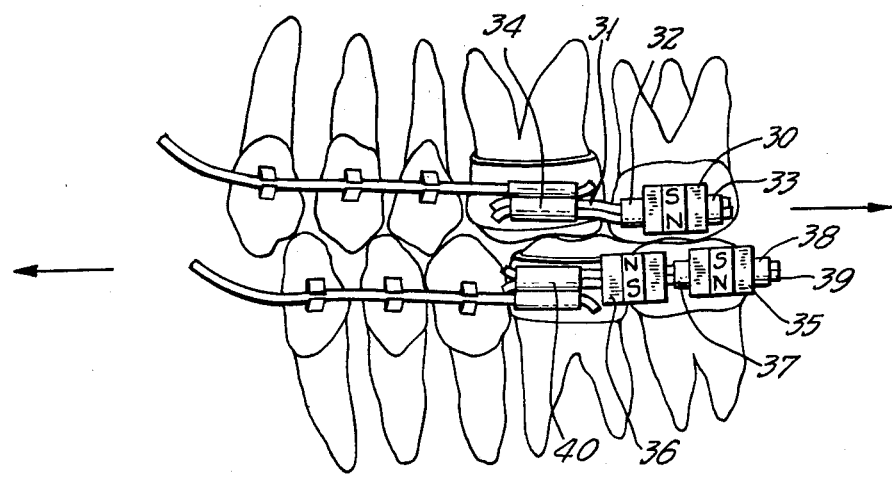
FIG. 4.
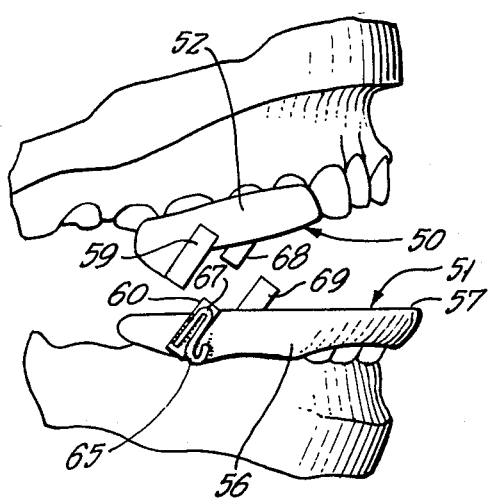
FIG. 5.
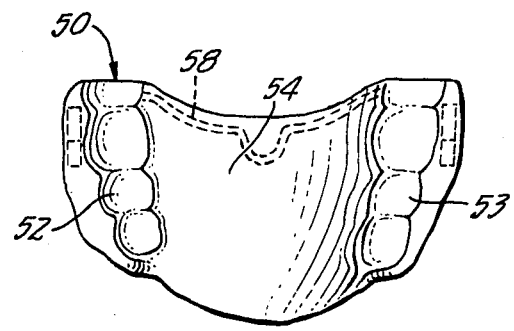
FIG. 6.
FIG. 7.
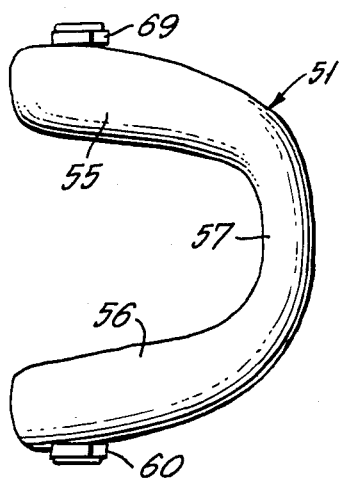
FIG. 9.
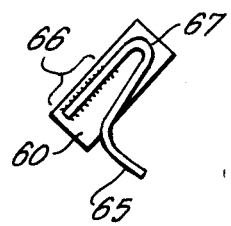
FIG. 10.
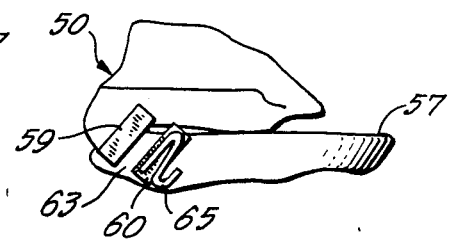
FIG. 8.

MAGNETIC FORCE FUNCTIONAL ORTHODONTIC APPLIANCES

BACKGROUND OF THE INVENTION

This application is a continuation-in-part of application Ser. No. 693,268, filed Jan. 22, 1985, for "Magnetic Force Orthodontic Kit and Appliances Constructed Therefrom now U.S. Pat. No. 4,593,361 issued June 17, 1986."

In said prior application, the disclosure of which is incorporated herein by reference, there are described inter alia several fixed appliance constructions for accomplishing Class II malocclusion correction. The fixed appliances are described as constructed with specially configured permanent magnets that are mounted on rectangular arch wires strung around the dental arches. In certain of the exemplary embodiments the magnetic modules are mounted with their planar pole faces parallel to a plane that is either inclined at an acute angle mesio-distally relative to the occlusal plane or is parallel to the occlusal plane thereby providing sufficient tolerance for mandibular movement without interference.

A removable appliance for intruding one or more teeth is described in U.S. Pat. No. 4,396,373, issued Aug. 2, 1983 and entitled "Magnetic Orthodontic Appliance." According to the patent abstract, the appliance described therein includes two separate rigid caps having internal shapes conforming to the crown portions of juxtaposed teeth in the maxilla and mandible, respectively. The caps are adapted to be removably frictionally secured to such teeth. Two permanent magnets carried by the two caps, respectively, having facing poles which are in registry when the mouth is normally closed, exert a magnetic force in a direction substantially normal to the occlusal plane. The poles are of extended area such that at least portions thereof remain in juxtaposed registry and the magnetic force remains substantially in the same direction for normal relative jaw movement. A modification is described in said patent of magnets placed on the occlusal surface of the teeth in the maxilla or mandible. In all of the illustrated embodiments, the opposing magnets have confronting poles with like-polarity such that the magnets repel and develop intrusive forces upon the respective teeth. In addition, there is a suggestion of bonding the appliances directly to the teeth and using dissimilar facing magnetic poles to attract and develop erupting forces on opposing teeth.

However, correction of Class II malocclusion involves, among other things, acting upon the mandible urging it anteriorly until the jaw muscles adapt and, if possible, until a certain amount of backward and upward growth of the condyle into the glenoid fossa occurs. In the process, teeth alignment may be corrected. This orthodontic procedure has been accomplished heretofore by use of various removable appliances, best known of which are the Frankel and Bionator devices. These appliances work on the principle of placing a physical barrier in the oral cavity constraining the mandible to move in a protrusive manner. They tend to be uncomfortable because they are bulky and force the mandible at the outset to advance immediately to the position of maximum protrusion. Since strict patient cooperation is required for effective treatment, the bulk, discomfort and inability to function normally contribute to poor compliance and, therefore, poor success.

Therefore, it is an object of the present invention to provide a less traumatic and more comfortable appliance for Class II malocclusion correction than those heretofore known.

It is a further object of the present invention to provide an appliance for inducing corrective protrusive repositioning in the treatment of Class II malocclusion, which appliance is provided with magnets for developing an elastic type of force operative parallel to the occlusal plane.

A still further object is to provide an appliance for the foregoing orthodontic procedure wherein magnets are so configured and located as to produce adequate corrective forces without unduly burdening the oral cavity.

SUMMARY OF THE INVENTION

In accordance with the present invention there is provided a magnetic force orthodontic appliance in which permanent magnet modules cooperate when installed within the oral cavity of a patient for exerting a selected force in a predetermined manner for inducing corrective protrusive repositioning in the treatment of Class II malocclusion, said appliance comprising in combination at least two prefabricated assemblies constructed for installation in an oral cavity, the first in force-coupled relation to the maxillary arch, and the second in force-coupled relation to the mandibular arch, and at least one set of permanent magnets mounted for confrontation, at least a first of said magnets being mounted on said first assembly and a second of said magnets being mounted on said second assembly, said first and second magnets each having one or more pole faces oriented relative to its associated assembly for assuming a position when installed in the oral cavity in which the pole faces of said first magnet align in complemental confrontation with the pole faces of said second magnet, said magnets being polarized and said pole faces being oriented for developing when in the oral cavity magnetic forces parallel to the occlusal plane for urging said second assembly anteriorly while reacting posteriorly on said first assembly for causing protrusion of the mandible relative to the maxillary arch.

BRIEF DESCRIPTION OF THE DRAWINGS

The invention will be better understood after reading the following detailed description of the presently preferred embodiments thereof with reference to the appended drawings in which:

FIG. 4 is an elevational view illustrating the use of three magnetic modules in "sliding" relationship for accomplishing Class II mechanics where increased force and travel is required over that available from two magnetic modules;

FIG. 5 is an elevational view illustrating a removable functional appliance provided with a plurality of magnetic modules mounted on a functional type base structure with the modules cooperating to accomplish Class II mechanics, the appliance being shown installed in relation to the dental arches with the jaws opened;

FIG. 6 is a top plan view of the maxillary component of the appliance of FIG. 5 showing the cavities for frictionally receiving the teeth of the maxillary arch;

FIG. 7 is a front elevational view of the maxillary component of FIG. 6;

FIG. 8 is a side elevational view of the two components of the appliance of FIG. 5 as they would appear with the jaws closed in centric and the mandible protruded;

FIG. 9 is a top plan view of the mandibular component of the appliance of FIG. 5 showing the location of the magnetic modules;

FIG. 10 is a fragmentary detail view showing wire mounting of a magnetic module for affording position adjustability;

The same reference numerals are used throughout the drawings to designate the same or similar parts.

DETAILED DESCRIPTION OF THE PRESENTLY PREFERRED EMBODIMENTS

Figure 1:
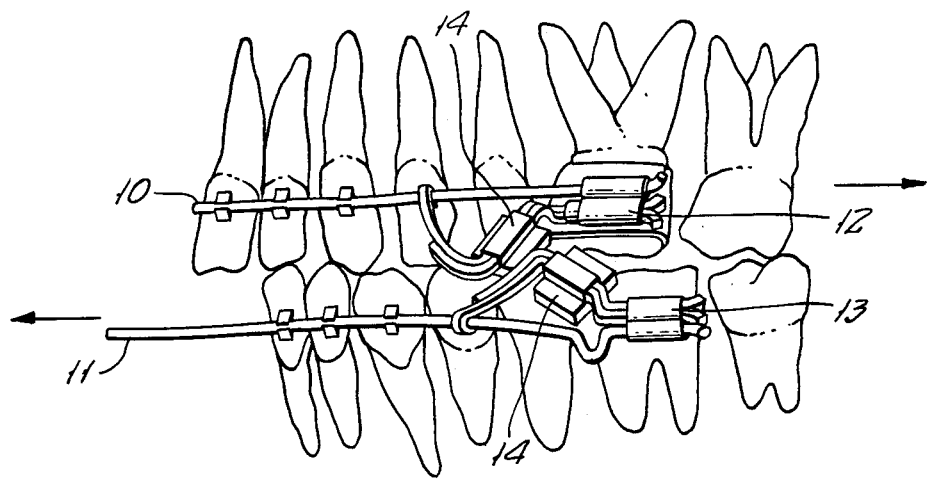
FIG. 1 is an elevational view illustrating an intermaxillary fixed appliance for correcting a Class II malocclusion constructed with arch wires and small specially constructed magnetic modules functioning in attraction.

Referring now to the drawings, and particularly to the embodiments illustrated in FIGS. 1 to 4, there are illustrated a number of exemplary fixed appliances that can be constructed using kit components described in detail in our prior application Ser. No. 693,268, along with standard orthodontic devices such as bands, tubes, base arch wires, arch wire brackets and so forth. As disclosed in said copending application, the various appliances are constructed utilizing small magnetic modules. The modules are rectangular prismatic formed from a cobalt-samarium alloy, covered with a chlorinated poly-p-xylylene coating or stainless steel and jacketed in stainless steel with orthogonally related passages on opposite sides having rectangular cross-sections for receiving with a snug fit the rectangular cross-section attachment wire.

As further explained in our copending application, the magnetic modules can be combined in various combinations relying on the attraction between unlike poles or repulsion between like poles. Because each module has two orthogonally related attachment wire receiving passages, the modules can be oriented conveniently with either pole face positioned to cooperate with an adjacent magnet.

Considering FIG. 1, there is illustrated therein an intermaxillary appliance with the magnets in attraction. Here, base arch wires 10 and 11 are installed in conventional manner on the upper and lower arches anchored to the first molars. Using oval, half round or other non-circular cross-section tubes 12 and 13, and attachment wires bent V-shape, the modules 14 are secured to the respective arches for drawing distally on the upper arch and, conversely, urging the lower arch mesially. The angled position of the modules 14 provides sufficient tolerance for mandibular movement without interference.

Figure 2:
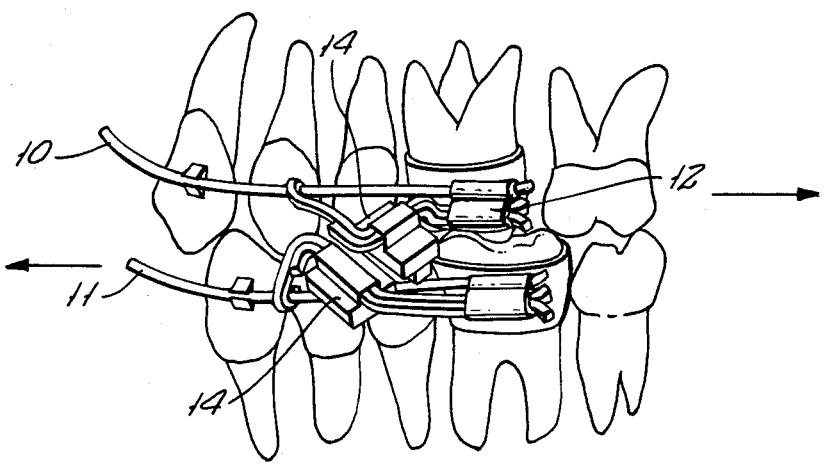
FIG. 2 is an elevational view illustrating a modification of the appliance of FIG. 1 with the magnetic modules functioning in repulsion.

FIG. 2 illustrates a reversal of the magnets 14 over that used in FIG. 1. In FIG. 2 the magnets 14 are acting in repulsion. Also because of the natural arc of mandibular motion, the modules can be arranged, if desired, to contact prematurely upon forceable closure of the jaw and thus contribute mechanically to the intended relative movement.

Frequently, the orthodontist desires to accomplish without too frequent readjustment of the appliance greater movement of the teeth than that provided with the appliances described above. For this purpose resort can be had to the principles underlying the appliance construction shown in FIGS. 3 and 4. For convenience, the relative motion between modules can be thought of as involving "sliding" motion although the relatively moving magnets may not actually be in physical contact. Thus, in FIG. 3, modules 20 and 21 are mounted, each with vertical polarization, respectively on the upper and lower dental arches. If unlike poles are facing each other, because of the horizontal offset of module 20 mesially and module 21 distally, the attractive force will have a vector parallel to the occlusal plane tending to move the segments in the directions of the respective arrows 22 and 23. With a vertical separation of 0.01 mm when the jaws are closed in centric relation, attractive forces ranging from 35 gm with 0.5 mm horizontal offset to 70 gm with 3.0 mm horizontal offset is easily obtained. The maximum available force falls off to 50 gm with a vertical separation of 0.5 mm and drops to 35 gm at 1.0 mm separation. However, it can be shown that a much more stable force is obtainable over a horizontal movement of about 2 mm, than can be obtained when relying on movement normal to the magnetic pole faces. Also, when positioned one over the other, controlled vertical forces are available to obtain bite opening if desired.

Figure 3:
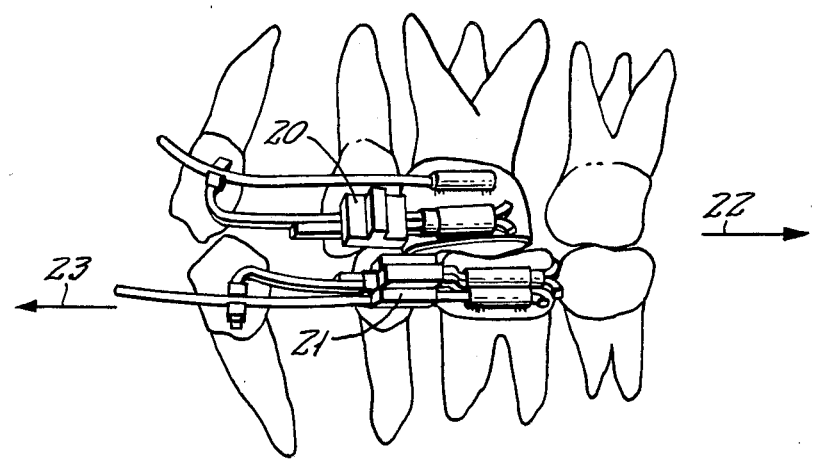
FIG. 3 is an elevational view illustrating the use of two magnetic modules in a fixed appliance in "sliding" relationship, the appliance constituting a further modification of the appliance of FIG. 1.

Summarizing, it will be seen from FIG. 3 that the two modules 20 and 21 have each a planar pole face of a given polarity confronting the pole face of the other substantially in parallel and with a predetermined gap therebetween in the direction normal to the surfaces of said pole faces. The respective axis of magnetic polarization of each of modules 20 and 21 is offset mesio-distally from the co-linear relationship such that there is developed between said modules a magnetic force having at least a vector component in a direction parallel to said pole faces. The mounting of the magnets in the appliance as illustrated in FIG. 3 is such as to prevent the modules from totally closing the gap therebetween as the jaw is closed, the purpose being to insure against frictional binding. However, it has been discovered that the presence of saliva between the pole faces provides sufficient lubrication to overcome friction even when the magnets are permitted to contact.

The movement assumed for the appliance of FIG. 3 is based on confrontation of unlike pole faces. However, reverse forces can be developed by having like polarity poles facing each other. This arrangement can be useful in correcting anterior open bite, cross-bite problems and vertical dysplasias.

Once the polarization axes depart from co-linearity, the separating force will have a vector component parallel to the confronting pole faces. This vector will tend to "slide" the modules either into or out of co-linearity depending upon whether the magnets are in attraction or repulsion.

The "sliding" principal can readily be extended to obtain increased forces and longer travel by adding modules as shown in FIG. 4. In the example of FIG. 4, a module 30, polarized as shown, is mounted on attachment wire 31, between crimped stops 32 and 33. The wire 31 is secured in the oval buccal tube 34 secured to the upper first molar by a suitable band. Confronting module 30 are modules 35 and 36 located by crimped stops 37 and 38 on attachment wire 39 secured in oval buccal tube 40. The modules 35 and 36 are poled as shown.

Reference should be had to our copending application identified above for a more complete discussion of the forces obtainable with various spacing between the magnetic modules.

As also explained in our aforesaid copending application, although all of the examples show the modules applied buccally to the dental arches, the modules can be installed lingually either as an alternative or in combination with a buccal construction. Use of both locations in consort will provide increased force, increased travel, or both, where desired.

An additional advantage derived from the sliding relationship of modules as exemplified in FIGS. 3 and 4 is the avoidance of interference with eccentric mandibular movement. However, in all embodiments wherein magnets are mounted one above the other but oriented and poled to develop a force horizontally, there is also a vertical force component, and such vertical force component must be taken into consideration by the orthodontist. Fortunately, it has been discovered that such vertical force can be usefully employed.

The embodiments illustrated in FIGS. 1 to 4 will be recognized as falling within the category of fixed appliances, however, the basic principle can be extended to removable appliances with a number of added advantages.

Referring now to FIGS. 5 to 9, there is illustrated a modified functional type of appliance in which a set of permanent magnets have been incorporated, mounted for confrontation. The maxillary component is designated generally by the reference numeral 50 while the mandibular component is designated generally by the numeral 51. As best seen in FIG. 6, the maxillary component 50 comprises bi-lateral tooth capping sections 52 and 53 joined by a palatal arch 54. Similarly, the mandibular component, best seen in FIG. 9, comprises bi-lateral tooth capping sections 55 and 56 joined by an anterior tooth capping section 57. Suitable reinforcing wire armature elements such as the element 58 in the palatal arch 54 may be included as required.

While conventional two-part functional appliances are normally constructed such that physical engagement between the maxillary and mandibular components constrain the mandible to a protrusive position, the present invention relies upon the forces developed by the various magnets incorporated therein. Thus, referring to FIGS. 5 to 10 there is shown a first magnet 59 mounted bucally on a flange portion of the section 52, and a second magnet 60 somewhat similarly mounted on the buccal flange of the tooth capping section 56 of the mandibular component 51. If the magnets are poled so that like magnetic poles confront across the gap 63, best seen in FIG. 8, the mandibular component 51 will be urged in the direction of the arrow 64 so as to enlarge the gap 63 within the constraints of the facial muscles.

In order to enable the orthodontist to adjust the spacing and orientation of the magnets within the oral cavity of the patient, at least certain of the magnets, such as the magnet 60, are mounted on interconnecting wires such as the wire 65 shown in detail in FIG. 10. As shown in FIG. 10, the wire is secured to the magnet by soldering or other known means within the end region indicated by the graphical brace 66. The remaining portion of the wire 65 is free and unbonded to the magnet to permit adjustment of the loop 67, thereby controlling the position of the magnet. The wire 65 normally would be attached mechanically to the armature wires within the associated assembly. It is to be understood that the assembly components 50 and 51 are generally constructed of a suitable plastic material.

To provide symmetry, another set of buccally located magnets are provided on the opposite side of the appliance, the magnet 68 appearing in both FIGS. 5 and 7, while the cooperating magnet 69 is shown in FIGS. 5 and 9. Although not shown in the drawings, additional magnets in pairs can be located, if desired, on the lingual side of the tooth capping portions of the functional base structures.

While the appliances heretofore known for accomplishing Class II malocclusion correction required the patient to reposition the mandible at an extreme protruded location whenever the appliance was placed in the mouth, the present invention applies elastic forces to accomplish this result gradually. Consequently, if complete forward protrusion of the mandible would discomfort the patient unduly, a compromise position will be attained with the mandible partially protruded and the muscle stresses balanced by the countervailing magnetic forces. Thus, the correction is brought about more gradually and with less discomfort to the patient. This encourages greater patient cooperation and quicker and better physiologic adaptation and growth.

The magnets in the embodiment illustrated in FIGS. 5 to 10 have planar pole faces and complementally confront one another with said pole faces parallel to a common plane which plane is inclined at an acute angle mesio-distally relative to the occlusal plane so as to permit relatively free mandibular articulation and function. However various other magnetic arrangements can be employed depending upon the forces desired as well as the amount of travel intended. A number of these variations are illustrated diagrammatically in FIGS. 11 to 20, inclusive, to which attention should now be directed.

Figure 11:
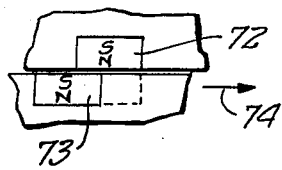
FIG. 11 is a diagrammatic illustration of the relationship of two magnetic modules when incorporated in a functional appliance for developing forces parallel to the occlusal plane.

In FIG. 11 there are shown two magnets 72 and 73 with dissimilar magnetic pole faces facing each other and with their respective magnetic axes offset mesio-distally in order to develop a force vector in the direction of the arrow 74 parallel to the occlusal plane.

Figure 12:
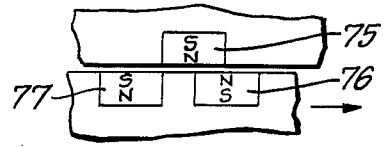
FIG. 12 is a diagrammatic illustration similar to FIG. 11 but showing the relationship of three magnetic modules for developing increased force and travel.

In FIG. 12, three magnets 75, 76 and 77 are utilized, offset as shown, for obtaining greater force and longer travel parallel to the occlusal plane.

Figure 13:
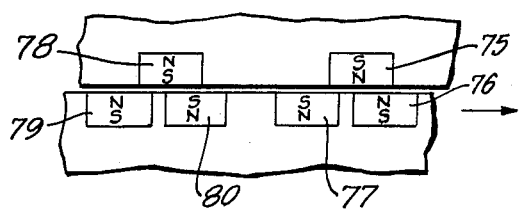
FIG. 13 is another diagram similar to FIG. 11 but showing two sets of three magnets each for developing twice the force of that provided with the embodiment of FIG. 12.

If still further force is required, the three magnet set shown in FIG. 12 can be duplicated as shown in FIG. 13 by adding the magnets 78, 79 and 80.

Figure 14:
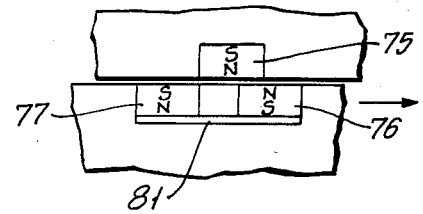
FIG. 14 is another diagram similar to FIG. 11 but showing the use of a low reluctance magnetic keeper for closing the magnetic circuit between two of the magnets of the embodiment of FIG. 12.

Instead of multiplying the number of magnets, increased magnetic force can be obtained by incorporating a keeper, a low reluctance "short circuit" path or element 81 bridging the free pole faces of the magnets 76 and 77, as shown in FIG. 14. Closing the magnetic circuit with a keeper will also decrease the external fringing field if this is desired ore required.

Figure 15:
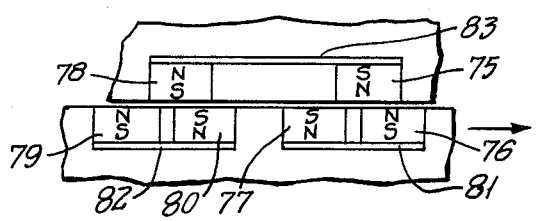
FIG. 15 is another diagram showing the addition of low reluctance magnetic keepers to the embodiment of FIG. 13.

In FIG. 15 keepers 81, 82 and 83 have been added to the magnets 75 to 80 of FIG. 13 with attendant increase in magnetic force available.

Figure 16:
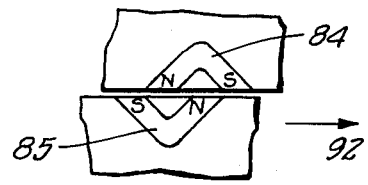
FIG. 16 is a diagrammatic illustration of the relationship between two generally L-shape magnets that cooperate to provide a substantially closed quadrilateral magnetic circuit.

In the embodiment of FIG. 16 the magnets are shown at 84 and 85 as being generally L-shape and arranged to cooperate to provide a substantially quadrilateral closed magnetic circuit when installed in an oral cavity and the jaws are closed in centric. With the polarity of the poles of the magnets 84 and 85 selected as shown in FIG. 16, the magnet 85 will tend to move in the direction of the arrow 92 in known manner.

Figure 17:
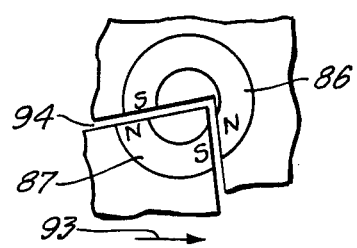
FIG. 17 is a diagrammatic illustration of yet another embodiment wherein the magnets are each annular and cooperate to provide a substantially circular closed magnetic circuit.
Figure 18:
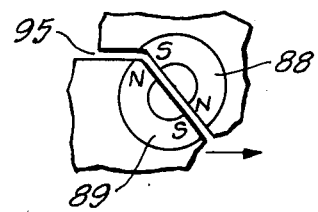
FIG. 18 is a diagrammatic illustration of a modification of the embodiment of FIG. 17.

In FIG. 17 the magnets 86 and 87 are shown as annular and cooperating to provide a substantially circular closed magnetic circuit when installed in an oral cavity and the jaws are closed. Although the attractive force is directed along a line inclined upwardly to the right as viewed in the drawing, the arrow 93 indicates the direction of motion of the magnet 87 relative to the magnet 86, bearing in mind the restraints imposed by the mounting in the oral cavity. Similarly, the magnets 88 and 89 in FIG. 18 are annular in configuration and cooperate to provide a substantially circular closed magnetic circuit. The principal difference between the embodiments of FIGS. 17 and 18 resides in the contouring of the gap 94 in FIG. 17, and the gap 95 in FIG. 18, the choice being dependent upon the forces desired and the relative interference encountered during mandibular movement.

Figure 19:
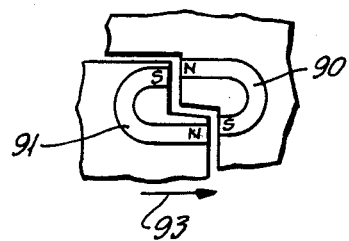
FIG. 19 is a diagrammatic illustration of an embodiment wherein the magnets are each J-shape and cooperate to provide a substantially parallel-sided oval closed magnetic circuit, the components being in the jaw closed in centric position.
Figure 20:
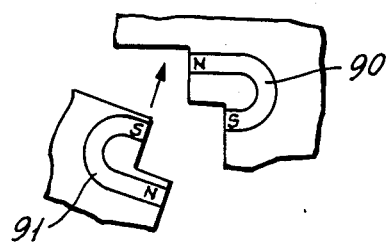
FIG. 20 is a view similar to FIG. 19, but with the components in the jaw opened position.

In FIGS. 19 and 20 a slightly different embodiment is illustrated wherein the magnets 90 and 91 are each J-shape and cooperate to provide a substantially parallel-sided oval closed magnetic circuit when installed in an oral cavity and the jaws are closed. The jaw closed position is shown in FIG. 19, and the jaw open position is shown in FIG. 20. As shown in FIG. 19, the magnet 91 will tend to travel in the direction of the arrow 96 relative to the magnet 90.

Figure 21:
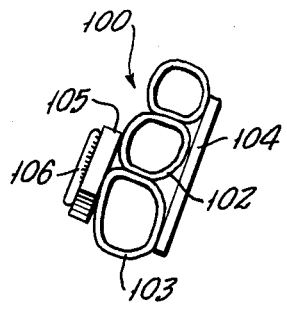
FIG. 21 is a top plan view of a prefabricated plural band structure with an associated magnetic module intended for construction of a fixed installation designed to perform Class II mechanics.
Figure 23:
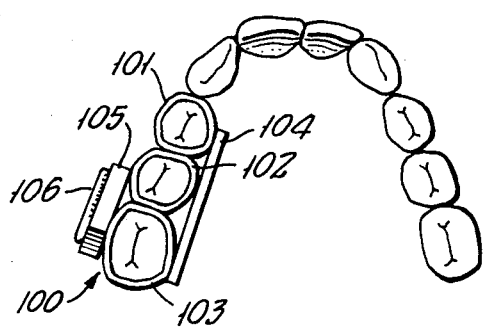
FIG. 23 is a plan view showing the structure of FIG. 21 fitted to teeth of one of the dental arches.
Figure 22:
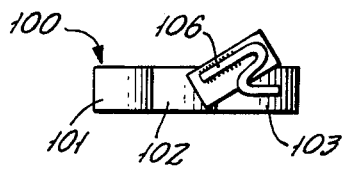
FIG. 22 is a side elevational view of the structure of FIG. 21.

The removable appliances described so far have all been based upon conventional functional type base structures. Such appliances are laboratory manufactured almost without exception. However, depending upon the patient requirements there may be an advantage of mounting the magnets for Class II mechanics directly upon the teeth of the dental arches. In such instance, prefabricated appliance components can be lab constructed such as the structure shown in FIGS. 21 to 23. Referring to said figures, there is shown a structure designated generally by the reference numeral 100 consisting of a plurality of metal bands 101, 102 and 103 that precisely fit certain teeth and that are secured together by soldering or the like and reinforced by an interconnecting bar 104. These bands can be fabricated by the laboratory based upon impressions furnished by the orthodontist and taken from the particular patient. As best seen in FIG. 22 a magnet 105 is mounted by wire 106 on the structure assembly of metal bands. The orthodontist can then install the structure 100 in the conventional manner upon the teeth in the dental arch as shown in FIG. 23. While not shown, a complementally cooperating structure can be mounted on the approximating molars of the opposing dental arch such that the confronting magnets cooperate in a manner similar to that described with reference to FIGS. 5 to 10, for example.

Figure 24:
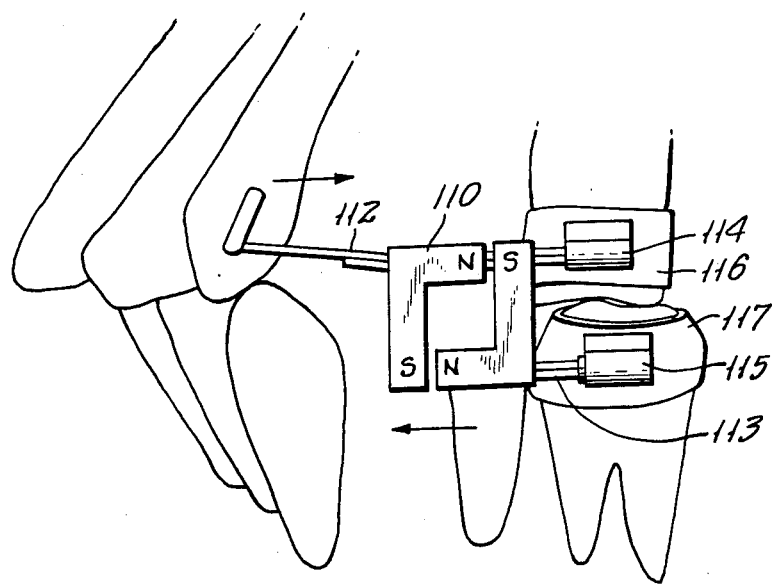
FIG. 24 is an elevational view of a fixed appliance as mounted on the teeth of the dental arches wherein the magnetic modules are L-shape for cooperating to provide a substantially closed magnetic circuit.
Figure 25:
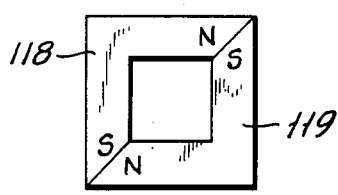
FIG. 25 is a view of two magnetic modules of L-shape, similar to those of FIG. 24, but with the module ends beveled to come together in a miter joint rather than the lap joint of FIG. 24.

The closed magnetic circuit principle as represented in the embodiments of FIGS. 14 to 20 can, of course, be extended to the fixed appliance configurations disclosed in our aforesaid copending application. Closing the magnetic circuit is one way to protect adjacent tissue from undesirable magnetic fields. More significant is the fact that the closed circuit maximizes the available force with minimum stray field. As an example, reference may be had to FIG. 24 wherein the two L-shape magnets 110 and 111 are mounted via arch wires 112 and 113 and non-circular buccal tubes 114 and 115 to molars via the bands 116 and 117. This arrangement produces an efficient closed magnetic circuit for repositioning a segment of the maxilla or for Class II mechanics. While a lap-butt arrangement is shown in FIG. 24, the ends of the magnets may be bevel cut as shown with reference to magnets 118 and 119 in FIG. 25. The bevel cut arrangement of FIG. 25 provides larger pole face area for increased force and is less likely to cause interference with mandibular movement as might be encountered with the construction of FIG. 24.

Figure 26:
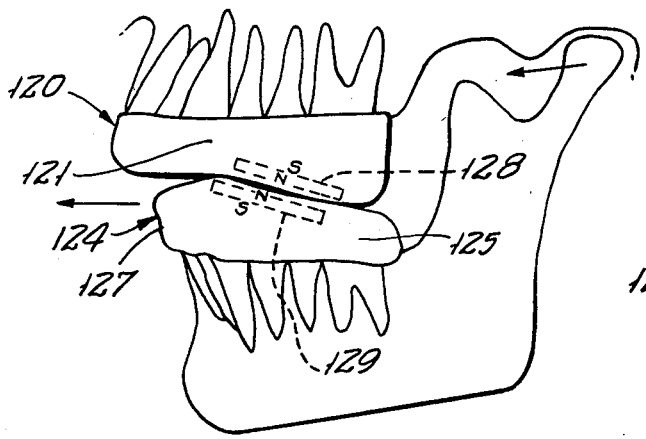
FIG. 26 is a view somewhat similar to that of FIG. 5, but in the jaw closed in centric position, showing a modified appliance in which the magnetic modules are of different construction and located at an inclination over the occlusal surfaces of the respective dental arches for protruding the mandible.
Figure 27:
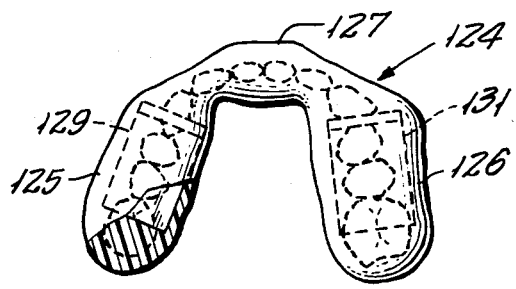
FIG. 27 is a plan view as seen from the occlusal plane of the mandibular component of the appliance of FIG. 26.
Figure 28:
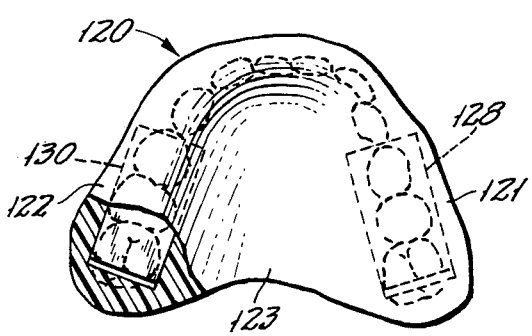
FIG. 28 is a plan view as seen from the occlusal plane of the maxillary component of the appliance of FIG. 26.

All of the embodiments of the present invention that have been described to this point employ magnets either buccally bilaterally or lingually bilaterally or both for accomplishing the work of a functional appliance, i.e., an appliance that serves to reposition or extend muscles and/or bone structure. Comparatively large forces are required for such procedure, the actual force depending upon the age of the patient; and in all cases, more force is needed for a functional procedure than would be needed merely to reposition teeth of the patient. Additionally, in performing a procedure to correct a Class II malocclusion where protrusion of the mandible is required, the appliance usually has to accommodate substantial movement or travel. Another appliance capable of providing the requisite force and travel is shown in FIGS. 26 to 28 wherein magnets are mounted bilaterally over the occlusal surfaces of the teeth. However, in order to provide for a horizontal force vector, the interpole-face gap is inclined mesio-distally. To provide for appreciable travel, long thin magnets are used at a shallow inclination.

Referring to FIGS. 26 to 28, there is shown an appliance consisting of maxillary and mandibular assemblies somewhat similar in base construction to the assemblies of the appliance described with reference to FIGS. 5 to 10. Thus, as seen in FIGS. 26 to 28, there is a first assembly 120 having bilateral tooth capping sections 121 and 122 joined by a palatal arch 123. Assembly 120 cooperates with a second assembly, 124, having bilateral tooth capping sections 125 and 126 joined by an aterior section 127.

Pairs of magnets, 128, 129 and 130, 131, are mounted in sets bilaterally within the respective tooth capping sections 121, 125, 122 and 126, as shown. One magnet of a pair, for example magnet 128, is mounted in the first assembly, 120, and the other magnet of the pair, magnet 129, is mounted in the second assembly, 124, the magnets being positioned within the assemblies for location between the occlusal surface of approximating posterior teeth of the dental arches. The magnets 128 to 131 are each in the form of a thin rectangular element magnetically polarized in the thickness direction and mounted in the respective assemblies, 120 and 124, such that when the appliance is in the oral cavity, like magnetic poles of each of the pairs of magnets will confront. The magnets constituting a pair are slightly displaced echelon-like relative to each other with those magnets that are in the second assembly, 124, namely magnets 129 and 131, being sufficiently anterior of the corresponding magnets 128 and 130 in the first assembly, 120, to ensure development, when in the oral cavity as seen in FIG. 26, of the necessary horizontal forces for urging the second assembly, 124, anteriorly.

When constructing the appliance of FIGS. 26 to 28, advantage can be taken of the fact that the jaws separate sufficiently without undue patient discomfort to tolerate up to about 10 mm. of appliance structure between approximating posterior molars. To obtain maximum force, the magnets 128 to 130 should be made as long as conveniently possible while maximizing the inclination relative to the occlusal plane, all within the constraints of permissable jaw separation. Obviously, a compromise relationship is required.

Figure 29:
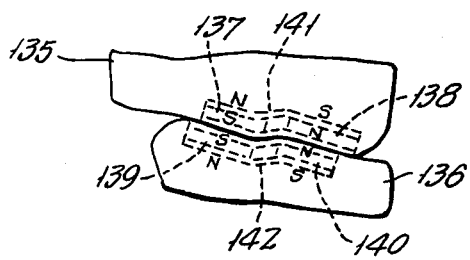
FIG. 29 is a side elevational view of an appliance similar to that of FIG. 26, but showing a closed magnetic circuit modification thereof.

On occasion it may be preferable to increase the number of magnets in the manner shown in FIG. 29 to which attention should now be directed. This figure illustrates a modification of the embodiment previously described with reference to FIGS. 26 to 28. Here, each of the tooth capping sections (only one side is illustrated, the other side being a mirror image) 135 and 136 includes two magnets 137, 138 and 139, 140, respectively. One of the two magnets, e.g., 137, is positioned anteriorly of the other magnet, i.e., 138. The two magnets in each tooth capping section are disposed to pair off with the two magnets in the opposing section of the other assembly. The two magnets, i.e., 137, 138 or 139, 140, within each tooth capping section, are oppositely poled magnetically and are joined by a low-reluctance bridge, 141 or 142, extending between those magnetic pole faces that are located closest to the tooth engaging surface of the respective appliance assembly to thereby produce a U-shape-like magnetic element. Each magnet of each U-shape-like element is inclined in the same direction mesio-distally and, when the assemblies are installed in an oral cavity, pairs of magnetic pole faces, in echelon in each tooth capping section, cooperate with each other in magnetic opposition to urge the mandibular assembly anteriorly relative to the maxillary assembly.

Figure 30:
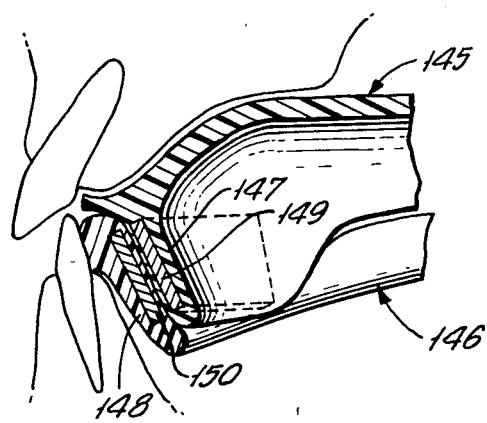
FIG. 30 is a mesio-distal vertical sectional view of a further embodiment of the present invention with magnets located in anterior flange portions of the respective appliance components.
Figure 31:
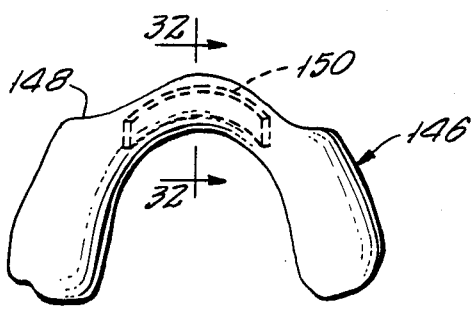
FIG. 31 is a plan view as seen from the occlusal plane of the mandibular component of the embodiment of FIG. 30.
Figure 32:
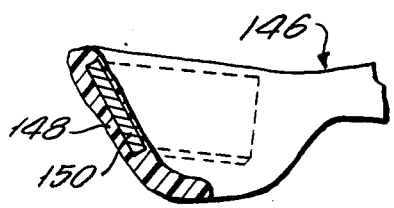
FIG. 32 is a fragmentary sectional view taken along the line 32—32 in FIG. 31.
Figure 33:
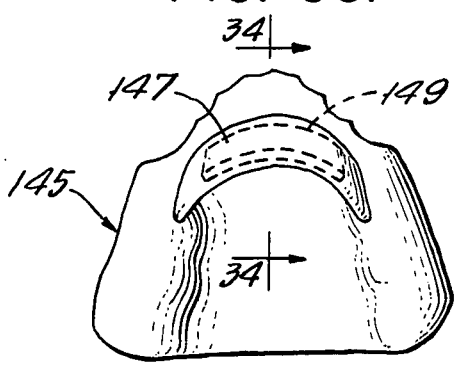
FIG. 33 is a plan view as seen from the occlusal plane of the maxillary component of the appliance embodiment of FIG. 30.
Figure 34:
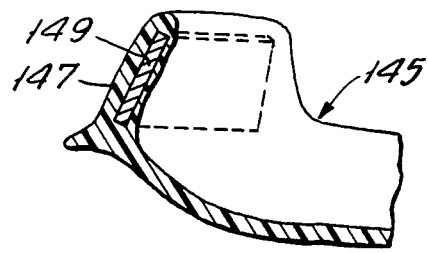
FIG. 34 is a fragmentary sectional view taken along the line 34—34 in FIG. 33.

Turning now to FIGS. 30 to 34, there is illustrated an appliance having a maxillary assembly 145 and a mandibular assembly 146, wherein the assemblies are provided with anterior flange portions, 147 and 148, respectively, that overlap when the assemblies 145 and 146 are installed in an oral cavity. This is best seen in FIG. 30 where it will be observed that the flange portion 147 on assembly 145 is positioned lingually of the flange portion 148 on assembly 146. Curved thin, generally rectangular, strips of magnetic material 149 and 150 are located, respectively, within the flange portions 147 and 148. As best seen from the diagrammatic illustration of FIG. 35, the magnet strips are polarized in the thickness direction. With like magnetic poles confronting, the separating force is oriented predominantly anteroposteriorly. As seen from FIGS. 30 to 34, the magnets 149 and 150 are located in the flanges 147 and 148 so as generally to parallel the anterior teeth of the respective dental arch. The ends of the magnets 149 and 150 generally will terminate at the first bicuspids. An advantage of the embodiment shown in FIGS. 30 to 34 is that it is possible to use larger magnetic elements and thereby obtain greater force.

Figure 35:
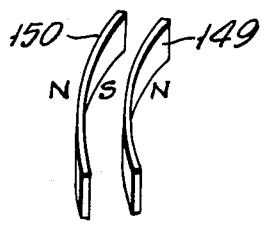
FIG. 35 is a diagrammatic illustration of two curved magnets which diagram is useful when explaining the construction and operation of the embodiment of FIG. 30.
Figure 36:
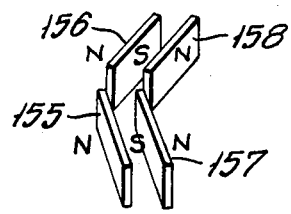
FIG. 36 is a view similar to FIG. 35 but illustrative of a modification thereof.
Figure 37:
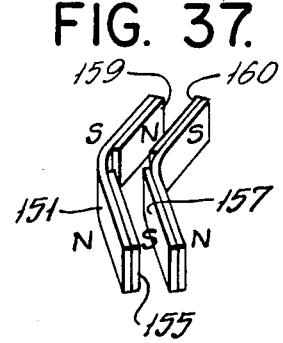
FIG. 37 is a view similar to FIG. 36 but showing yet another modification of the invention.

FIG. 35 shows the manner in which the curved or arcuate magnets 149 and 150 cooperate to provide a strong horizontal force tending to separate the magnets. However, instead of one-piece magnets 149 and 150, similar results can be obtained by substituting separate flat magnetic elements 155, 156, 157 and 158 disposed in the manner shown diagrammatically in FIG. 36. Alternatively, the polarities of one cooperating pair, e.g., 159, 160, can be reversed as shown in FIG. 37. In addition, keepers 151 and 152 join the anterior facing poles of magnets 155 and 159, and the posterior facing poles of magnets 157 and 160, respectively. This may be preferable to that of FIG. 36 because it results in a magnetic circuit that tends to be closed as compared with FIG. 36 and, therefore, will have less magnetic field spreading posteriorly, and somewhat greater coercive force.

Figure 38:
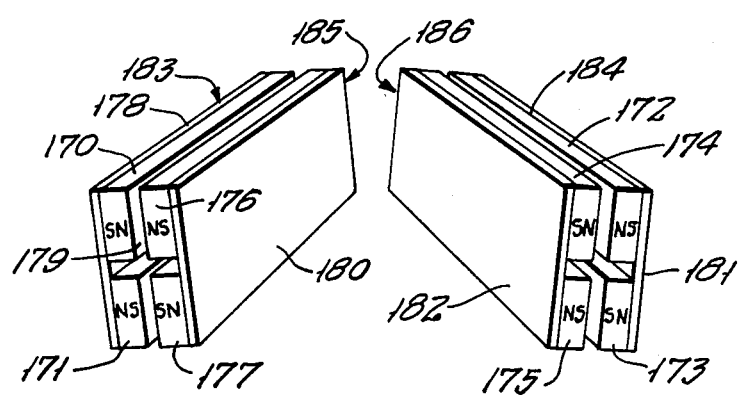
FIG. 38 is a diagrammatic illustration of a series of flat magnets joined in pairs by low reluctance keepers and representing a modification of the embodiment represented by the illustration in FIG. 36.

The principles illustratively implemented in the embodiments previously described with reference to FIGS. 13 to 15, namely, that increased force can be obtained by increasing the number of small magnets and that further force can be obtained by bridging with a keeper the magnetic poles that are remote from the operating gap, can also be applied to the embodiments of FIGS. 30 to 37. By way of example there is shown in FIG. 38 a modification of the embodiment of FIG. 36. Instead of the four magnets 155 to 158, eight magnets, 170 to 177, are employed with polarities such as that shown. A thin sheet of low magnetic reluctance material 178 is joined to those pole faces of magnets 170 and 171 that are remote from the working gap 179. Similarly, the remote poles of magnets 176 and 177 are joined by the keeper 180. Magnets 172 and 173 are joined by a similar keeper 181, while magnets 174 and 175 are joined by a keeper 182. The resultant "horseshoe" magnet structures 183, 184, 185 and 186 can be related in terms of general function and placement within the oral cavity to the magnets 155, 156, 157 and 158, respectively, in FIG. 36. However, the force tending to separate the magnet structures 183 and 184 from the structures 185 and 186 is more than double that available with the FIG. 36 embodiment.

It should be understood that FIGS. 35 to 38 are greatly enlarged and exaggerated in order to facilitate illustration. In FIG. 38, for example, the left and right sets of magnets would more likely converge at an obtuse rather than acute angle, more like that seen in FIGS. 36 and 37.

Having described the presently preferred embodiments of the invention with reference to the appended drawings, it will be understood by those skilled in the art that various changes in construction can be introduced without departing from the true spirit of the invention as defined in the appended claims.

We claim:

1. A magnetic force othodontic appliance in which permanent magnet modules cooperate when installed within the oral cavity of a patient for exerting a selected force in a predetermined manner for inducing corrective protrusive repositioning in the treatment of Class II malocclusion, said appliance comprising in combination at least two prefabricated assemblies constructed for installation in an oral cavity, said assemblies including respective means for joining the first assembly in force-coupled relation to teeth of the maxillary arch, and the second assembly in force-coupled relation to teeth of the mandibular arch, and at least one set of permanent magnets mounted for confrontation, at least a first of said magnets being mounted on said first assembly and a second of said magnets being mounted on said second assembly, said first and second magnets each having one or more pole faces oriented relative to its associated assembly for assuming a position when installed in the oral cavity in which the pole faces of said first magnet align in complemental confrontation with the pole faces of said second magnet, said magnets being polarized and said pole faces being oriented for developing when in the oral cavity magnetic forces parallel to the occlusal plane for urging said second assembly anteriorly while reacting posteriorly on said first assembly for causing protrusion of the mandible relative to the maxillary arch.

2. A magnetic force orthodontic appliance according to claim 1, wherein said first assembly comprises bilateral tooth capping sections joined by a palateral arch, and said second assembly comprises bilateral tooth capping sections joined by an anterior section, said tooth capping sections providing said means for joining said assemblies to said teeth.

3. A magnetic force orthodontic appliance according to claim 2, wherein said sets of magnets comprise pairs of magnets with said sets mounted bilaterally respectively on the buccal and/or lingual sides of said tooth capping sections with the magnets of each pair separately mounted on the first and second assemblies, respectively, for mutual cooperation.

4. A magnetic force orthodontic appliance according to claim 3, wherein each of said magnets has a planar pole face, and said complemental confrontation occurs with said planar pole faces parallel to a common plane which plane is inclined at an acute angle mesio-distally relative to the occlusal plane so as to permit relatively free mandibular articulation and function.

5. A magnetic force orthodontic appliance according to claim 4, wherein said planar pole faces are spaced from said common plane in the direction normal thereto, and are of opposite magnetic polarity, and said assemblies maintain a magnetically effective inter-pole-face separation between said magnets to develop said corrective force.

6. A magnetic force orthodontic appliance according to claim 4, wherein said planar pole faces are of opposite magnetic polarity, and said assemblies maintain a magnetically effective inter-pole-face proximity to develop said corrective force.

7. A magnetic force orthodontic appliance according to claim 1, wherein at least certain of said magnets are joined to said assemblies by individual position adjustable interconnecting elements.

8. A magnetic force orthodontic appliance according to claim 2, wherein at least certain of said magnets are joined to said plate type assembly by individual position adjustable interconnecting elements.

9. A magnetic force orthodontic appliance according to claim 3, wherein at least certain of said magnets are joined to said plate type assembly by individual position adjustable interconnecting elements.

10. A magnetic force orthodontic appliance according to claim 4, wherein at least certain of said magnets are joined to said plate type assembly by individual position adjustable interconnecting elements.

11. A magnetic force orthodontic appliance according to claim 1, wherein at least one of said first and second magnets has two pole faces both positioned for confronting at least one pole face of the other magnet, said two pole faces being joined by low reluctance magnetic material to form a closed magnetic circuit between said two pole faces on one side thereof.

12. A magnetic force orthodontic appliance according to claim 11, wherein said other magnet has two pole faces postioned to confront respectively a corresponding one of the two pole faces of said at least one magnet, and low reluctance magnetic material joins the two pole faces of said other magnet on one side thereof to provide a closed magnetic circuit.

13. A magnetic force orthodonic appliance according to claim 12, wherein said first and second magnets are each J-shape and cooperate to provide a substantially parallel-sided oval closed magnetic circuit when installed in an oral cavity and the jaws are closed in centric.

14. A magnetic force orthodontic appliance according to claim 12, wherein said first and second magnets are each annular and cooperate to provide a substantially circular closed magnetic circuit when installed in an oral cavity and the jaws are closed in centric.

15. A magnetic force orthodontic appliance according to claim 12, wherein said first and second magnets are each generally L-shape and cooperate to provide a substantially quadrilateral closed magnetic circuit when installed in an oral cavity and the jaws are closed in centric.

16. A magnetic force orthodontic appliance in which permanent magnet modules cooperate when installed within the oral cavity of a patient for exerting a selected force in a predetermined manner for inducing corrective protrusive repositioning in the treatment of Class II malocclusion, said appliance comprising in combination at least two prefabricated assemblies constructed for installation in an oral cavity, said assemblies including respective means for joining the first assembly in force-coupled relation to teeth of the maxillary arch, and the second assembly in force-coupled relation to teeth of the mandibular arch, and at least one set of permaent magnets mounted for confrontation, at least a first of said magnets being mounted on said first assembly and a second of said magnets being mounted on said second assembly, said first and second magnets each having one or more pole faces oriented relative to its associated assembly for assuming a position when installed in the oral cavity in which the pole faces of said first magnet align in complemental confrontation with the pole faces of said second magnet, each of said first and second magnets having a planar pole face, and said complemental confrontation occurs with said planar pole faces parallel to a common plane which plane is inclined at an acute angle mesio-distally relative to the occlusal plane so as to permit relatively free mandibular articulation and function, said magnets being polarized and said pole faces being oriented for developing when in the oral cavity magnetic forces parallel to the occlusal plane for urging said second assembly anteriorly while reacting posteriorly on said first assembly for causing protrusion of the mandible relative to the maxillary arch.

17. A magnetic force orthodontic appliance according to claim 16, wherein said planar pole faces are spaced from said common plane in the direction normal thereto, and are of opposite magnetic polarity, and said assemblies maintain a magnetically effective inter-pole-face separation between said magnets to develop said corrective force.

18. A magnetic force orthodontic appliance according to claim 16, wherein said planar pole faces are of opposite magnetic polarity, and said assemblies maintain a magnetically effective inter-pole-face proximity to develop said corrective force.

19. A magnetic force orthodontic appliance in which permanent magnet modules cooperate when installed within the oral cavity of a patient for exerting a selected force in a predetermined manner for inducing corrective protrusive repositioning in the treatment of Class II malocclusion, said appliance comprising in combination at least two prefabricated assemblies the first of which is constructed for installation about one or more of the posterior teeth of the maxillary arch, and the second of which is constructed for installation about at least the posterior teeth of the mandibular arch that occlude with said one or more teeth of the maxilary arch, and at least one set of permanent magnets mounted for confrontation, at least a first of said magnets being mounted on said first assembly and a second of said magnets being mounted on said second assembly, said first and second magnets each having a planar pole face of a given polarity oriented relative to its associated assembly for assuming a position when installed in the oral cavity in which said pole faces are substantially parallel to a common plane and in mutual magnetic force relationship, said common plane being inclined at an acute angle mesio-distally relative to the occlusal plane so as to permit relatively free mandibular articulation and function while developing a corrective force substantially parallel to the occlusal plane for causing protrusion of the mandible relative to the maxillary arch.

20. A magnetic force orthodontic appliance according to claim 19, wherein said pole faces are spaced from said common plane in the direction normal thereto, said pole faces are of opposite magnetic polarity, and said assemblies maintain a magnetically effective inter-pole-face separation between said magnets to develop said corrective force.

21. A magnetic force orthodontic appliance according to claim 19, wherein said pole faces are of opposite magnetic polarity, and said assemblies maintain a magnetically effective inter-pole-face proximity to develop said corrective force.

22. A magnetic force orthodontic appliance according to claim 19, wherein said magnets are secured to the flanges of a plate type assembly having one or more cavities for receiving said teeth.

23. A magnetic force orthodontic appliance according to claim 22, wherein said plate type assembly is dimensioned to receive said teeth in said cavities with a friction fit.

24. A magnetic force orthodontic appliance according to claim 23, wherein at least certain of said magnets are joined to said plate type assembly by individual position adjustable interconnecting elements.

25. A magnetic force orthodontic appliance according to claim 22, wherein at least certain of said magnets are joined to said plate type assembly by individual position adjustable interconnecting elements.

26. A magnetic force orthodontic appliance according to claim 19, wherein said magnets are each secured to a corresponding plurality of dental bands that are joined together and prefabricated for fixed installation directly on the teeth of the patient.

27. A magnetic force orthodontic appliance according to claim 26, wherein at least certain of said magnets are joined to said bands by individual position adjustable interconnecting elements.

28. A magnetic force orthodontic appliance according to claim 16, wherein said first and second magnets are mounted on said respective assemblies for location between the occlusal surfaces of approximating posterior teeth of the dental arches.

29. A magnetic force orthodontic appliance according to claim 28, wherein said first and second magnets are thin rectangular elements magnetically polarized in the thickness direction and mounted on said respective assemblies with like magnetic poles arranged for confrontation and being slightly displaced echelon-like with said second magnet sufficiently anterior of said first magnet to ensure development when in the oral cavity of said magnetic forces for urging said second assembly anteriorly.

30. A magnetic force orthodontic appliance according to claim 2, wherein said first and second magnets are mounted on said respective assemblies for location between the occlusal surfaces of approximating posterior teeth of the dental arches.

31. A magnetic force orthodontic appliance according to claim 2, wherein said sets of magnets comprise pairs of magnets with said sets mounted bilaterally with the individual magnets within the tooth capping sections of said assemblies with one magnet of a pair in the first assembly and the other magnet of the pair in the second assembly for location between the occlusal surfaces of approximating posterior teeth of the dental arches, said magnets being thin rectangular elements magnetically polarized in the thickness direction and mounted in said respective assemblies with like magnetic poles of each said pair of magnets for confrontation and being slightly displaced echelon-like with the magnets of said pairs that are in said second assembly sufficiently anterior of the corresponding magnets in said first assembly to ensure development when in the oral cavity of said magnetic forces for urging said second assembly anteriorly.

32. A magnetic force orthodontic appliance according to claim 31, wherein each of said tooth capping sections includes two of said magnets located with one of said two magnets positioned anteriorly of the other, the two magnets in each tooth capping section being disposed to pair off with the two magnets in the opposing tooth capping section of the other assembly, each said two magnets being oppositely poled magnetically and being joined by a low reluctance bridge between those pole faces that are located closest to the tooth engaging surface of the respective assembly to thereby produce a U-shape-like magnetic element, each magnet of each said magnet element being inclined in the same direction mesio-distally, whereby when said assemblies are installed in an oral cavity pairs of pole faces in echelon in each tooth capping section cooperate with each other in magnetic opposition to urge said second assembly anteriorly relative to said first assembly.

33. A magnetic force orthodontic appliance according to claim 1, wherein said assemblies are provided with anterior flange portions that overlap when the assemblies are installed in an oral cavity, the flange portion on said first assembly being positioned distally of said flange portion on said second assembly, and said first and second magnets are located respectively in said flange portions with magnetic polarization oriented predominantly mesio-distally and in magnetic repulsion as between said magnets.

34. A magnetic force orthodontic appliance according to claim 33, wherein said first and second magnets are each formed from thin curved strips of magnetic material polarized in the thickness direction, said strips generally paralleling the anterior teeth of the respective dental arch.

35. A magnetic force orthodontic appliance in which permanent magnet modules are supported on attachment wires for installation within the oral cavity adapted to be coupled to teeth of the maxillary and mandibular arches for exerting a selected force in a predetermined manner for accomplishing a desired orthodontic procedure, comprising in combination supported on attachment wires at least three such modules each having a planar pole face of a given polarity, two of said modules being mounted in side-by-side relationship for disposition adjacent one dental arch with their respective pole faces lying in a common plane, and the third module being mounted for disposition adjacent the other dental arch on the opposite side of said plane from said first two modules spaced from said plane in the direction normal thereto by a predetermined gap and with its pole face parallel to said plane, said three modules being magnetically polarized and located relative to each other such that magnetic forces are exerted between said third module and said two other modules tending to translate said third module by a combination of attraction and repulsion to and from one and the other, respectively, of said first two modules, and means preventing said modules from closing said gap thereby constraining said modules to translate mesio-distally relative to each other.

36. A magnetic force orthodontic appliance in which permanent magnet modules are supported on attachment wires for installation within the oral cavity adapted to be coupled to teeth of the maxillary and mandibular arches for exerting a selected force in a predetermined manner for accomplishing a desired orthodontic procedure, comprising in combination supported on attachment wires at least three such modules each comprising a body of permanently magnetized material having a planar pole face of a given polarity and means defining at least two orthogonally related through passages of non-circular cross-section, two of said modules being mounted in side-by-side relationship for disposition adjacent one dental arch with their respective pole faces lying in a common plane, and the third module being mounted for disposition adjacent to the other dental arch on the opposite side of said plane from said first two modules spaced from said plane in the direction normal thereto by a predetermined gap and with its pole face parallel to said plane, said attachment wires having a non-circular cross-section and passing through at least one of said passages of each of said modules for mounting said module, the shape and size of said passages and wires being such as to preclude rotation of said modules about said wires, said three modules being magnetically polarized and located relative to each other such that magnetic forces are exerted between said third module and said other modules tending to translate said third module by a combination of attraction and repulsion to and from one and the other, respectively, of said first two modules, and means preventing said modules from closing said gap thereby constraining said modules to translate mesio-distally relative to each other.

37. A magnetic force orthodontic appliance according to claim 36, characterized in that each of said attachment wires comprises two lengths of edgwise wire bonded together side-by-side, and each of said passages has a substantially rectangular cross-section.

* * * * *